(12) United States Patent
Avery et al.

(10) Patent No.: US 9,974,907 B2
(45) Date of Patent: May 22, 2018

(54) CODING SYSTEM FOR A DRUG DELIVERY DEVICE AND DRUG DELIVERY DEVICE

(75) Inventors: Richard James Vincent Avery, Chipping Campden (GB); Joseph Butler, Rugby (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 599 days.

(21) Appl. No.: 13/813,677

(22) PCT Filed: Aug. 11, 2011

(86) PCT No.: PCT/EP2011/063845
§ 371 (c)(1),
(2), (4) Date: May 13, 2013

(87) PCT Pub. No.: WO2012/020087
PCT Pub. Date: Feb. 16, 2012

(65) Prior Publication Data
US 2013/0218078 A1    Aug. 22, 2013

Related U.S. Application Data

(60) Provisional application No. 61/373,378, filed on Aug. 13, 2010.

(30) Foreign Application Priority Data

Oct. 26, 2010 (EP) .................................... 10188853

(51) Int. Cl.
*A61M 5/50* (2006.01)
*A61M 5/24* (2006.01)
*A61M 5/315* (2006.01)

(52) U.S. Cl.
CPC ............. *A61M 5/5086* (2013.01); *A61M 5/24* (2013.01); *A61M 5/315* (2013.01); *A61M 5/31553* (2013.01); *A61M 2205/6045* (2013.01)

(58) Field of Classification Search
CPC ........ A61M 2205/6045; A61M 5/5086; A61M 5/24; A61M 2005/2403;
(Continued)

(56) References Cited

U.S. PATENT DOCUMENTS

| 533,575 A | 2/1895 | Wilkens |
|---|---|---|
| 5,226,895 A | 7/1993 | Harris |

(Continued)

FOREIGN PATENT DOCUMENTS

| EP | 0937471 A2 | 8/1999 |
|---|---|---|
| EP | 0937476 A2 | 8/1999 |

(Continued)

OTHER PUBLICATIONS

English Translation of Notice of Reasons for Rejection Issued in Japanese Patent Application No. 2013-523619 dated Apr. 14, 2015.
(Continued)

*Primary Examiner* — Bhisma Mehta
*Assistant Examiner* — Jenna Zhang
(74) *Attorney, Agent, or Firm* — McDonnell Boehnen Hulbert & Berghoff LLP

(57) ABSTRACT

A coding system for a drug reservoir, where the drug reservoir is intended for use with a reservoir holder of a drug delivery device. The coding system includes a collar fitted around the drug reservoir. The collar includes a coding feature that is configured to pass through a corresponding coding feature provided by the reservoir holder of the drug delivery device.

9 Claims, 4 Drawing Sheets

(58) Field of Classification Search
CPC .. A61M 2005/2433; A61M 2005/2407; A61M 5/31553; A61M 5/315
See application file for complete search history.

(56) References Cited

U.S. PATENT DOCUMENTS

| | | | |
|---|---|---|---|
| 5,279,586 A | | 1/1994 | Balkwill |
| 5,304,152 A | | 4/1994 | Sams |
| 5,320,609 A | | 6/1994 | Haber et al. |
| 5,334,162 A | * | 8/1994 | Harris .................. A61J 1/062 604/232 |
| 5,383,865 A | | 1/1995 | Michel |
| 5,480,387 A | | 1/1996 | Gabriel et al. |
| 5,505,704 A | | 4/1996 | Pawelka et al. |
| 5,554,134 A | * | 9/1996 | Bonnichsen ........... A61M 5/24 604/232 |
| 5,582,598 A | | 12/1996 | Chanoch |
| 5,626,566 A | | 5/1997 | Petersen et al. |
| 5,674,204 A | | 10/1997 | Chanoch |
| 5,688,251 A | | 11/1997 | Chanoch |
| 5,921,966 A | | 7/1999 | Bendek et al. |
| 5,961,495 A | | 10/1999 | Walters et al. |
| 6,004,297 A | | 12/1999 | Steenfeldt-Jensen et al. |
| 6,193,698 B1 | | 2/2001 | Kirchhofer et al. |
| 6,221,046 B1 | | 4/2001 | Burroughs et al. |
| 6,235,004 B1 | | 5/2001 | Steenfeldt-Jensen et al. |
| 6,248,095 B1 | | 6/2001 | Giambattista et al. |
| 6,899,698 B2 | | 5/2005 | Sams |
| 6,936,032 B1 | | 8/2005 | Bush, Jr. et al. |
| 7,241,278 B2 | | 7/2007 | Moller |
| 2002/0052578 A1 | | 5/2002 | Moller |
| 2002/0120235 A1 | | 8/2002 | Enggaard |
| 2003/0050609 A1 | | 3/2003 | Sams |
| 2003/0078195 A1 | * | 4/2003 | Kristensen ............. A61M 5/24 604/201 |
| 2004/0059299 A1 | | 3/2004 | Moller |
| 2004/0210199 A1 | | 10/2004 | Atterbury et al. |
| 2004/0243065 A1 | * | 12/2004 | McConnell ........... A61J 1/2096 604/183 |
| 2004/0267207 A1 | | 12/2004 | Veasey et al. |
| 2005/0113765 A1 | | 5/2005 | Veasey et al. |
| 2006/0153693 A1 | | 7/2006 | Fiechter et al. |
| 2009/0099523 A1 | * | 4/2009 | Grant ................. A61M 5/14244 604/151 |
| 2009/0259197 A1 | * | 10/2009 | Christiansen ........... A61M 5/24 604/208 |
| 2009/0275916 A1 | | 11/2009 | Harms et al. |
| 2011/0152781 A1 | * | 6/2011 | Brunnberg .......... A61M 5/3129 604/189 |
| 2013/0204187 A1 | * | 8/2013 | Avery ..................... A61M 5/24 604/111 |
| 2013/0253432 A1 | * | 9/2013 | Avery ..................... A61M 5/24 604/187 |

FOREIGN PATENT DOCUMENTS

| | | | | |
|---|---|---|---|---|
| JP | | 2002360692 A | 12/2002 | |
| WO | | 9938554 A1 | 8/1999 | |
| WO | | 0110484 A1 | 2/2001 | |
| WO | | 03017915 A1 | 3/2003 | |
| WO | | 2005018721 A1 | 3/2005 | |
| WO | WO | 2008000827 A1 * | 1/2008 | .............. A61M 5/24 |
| WO | | 2008025772 A1 | 3/2008 | |
| WO | | 2010006870 A1 | 1/2010 | |
| WO | WO | 2011131777 A1 * | 10/2011 | .............. A61M 5/24 |

OTHER PUBLICATIONS

English Translation of Third Office Action issued in Chinese Patent Application No. 201180049541.8 dated Jul. 1, 2015.
Form PCT/ISA/220, Notification of Transmittal of the International Search Report and the Written Opinion of the International Searching Authority, or the Declaration, dated Nov. 7, 2011.
English Translation of Decision of Final Rejection of the Application issued in Chinese Patent Application No. 201180049541.8 dated Feb. 26, 2016.

\* cited by examiner

CODING SYSTEM FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. § 371 of International Application No. PCT/EP2011/063845 filed Aug. 11, 2011, which claims priority to U.S. Patent Application No. 61/373,378 filed Aug. 13, 2010 and European Patent Application No. 10188853.5 filed Oct. 26, 2010. The entire disclosure contents of these applications are herewith incorporated by reference into the present application.

FIELD OF INVENTION

The present patent application is generally directed to drug delivery devices and reservoirs, particularly reservoirs containing a medicament. More particularly, the present application is generally directed to a coding system for drug delivery device components and reservoirs so as to prevent unwanted cross use. As just one example, such medicament reservoirs may comprise an ampoule, a cartridge, a vial, or a pouch, and may be used with a medical delivery device. Exemplary medical delivery devices include, but are not limited to syringes, pen type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder is disconnected from the drug delivery device and the empty cartridge is removed and replaced with a new cartridge. Most suppliers of such cartridges recommend that the user dispose of the empty cartridges properly. Where the drug delivery device comprises a disposable device, once the cartridge is empty, the user is recommended to dispose of the entire device.

Such known self administration systems requiring the removal and reloading of empty cartridges have certain limitations. For example, in certain generally known systems, a user simply loads a new cartridge into the delivery system without the drug delivery device or without the cartridge having a mechanism of preventing cross use of an incorrect cartridge. That is, the drug delivery device does not have a mechanism for determining if the medicament contained in the cartridge is indeed the correct type of medicament to be administered by the patient. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and manufactured to comply with certain recognized local and international standards. Consequently, such cartridges are typically supplied in standard sized cartridges (e.g., 3 ml cartridges). Therefore, there may be a variety of cartridges supplied by a number of different suppliers and containing a different medicament but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

SUMMARY

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code a cartridge to its drug type and design an injection device that accepts or works with the dedication or coded features provided on or with the cartridge so as to prevent unwanted cartridge cross use. Similarly, there is also a general need for a dedicated cartridge that allows the medical delivery device to be used with an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e., making it more difficult for counterfeiters to provide unregulated counterfeit medicament carrying products.

It is an object of the invention to secure a correct use of drug reservoirs or cartridges in conjunction with a drug delivery device and to avoid an incorrect selection of a drug reservoir.

This object is achieved with the coding system according to claim 1 and with the drug delivery system according to claim 13, respectively. Further embodiments derive from the dependent claims.

According to an exemplary arrangement, a coding system for a drug reservoir is provided, where the drug reservoir is intended for use with a reservoir holder of a drug delivery device. The coding system includes a collar fitted around the drug reservoir, and this collar comprises a coding feature. The coding feature is configured to pass through a corresponding coding feature provided by the reservoir holder of the drug delivery device.

In another arrangement, a coding system for a drug delivery device includes a first feature, particularly a first ring feature, comprising a first coding feature and a second ring feature comprising a second coding feature. The first feature is fitted to a first component of the drug delivery device, particularly a dose setting mechanism or a drug reservoir or cartridge, and the second ring feature is fitted to a second component of the drug delivery device, particularly a reservoir holder. The first coding feature and the second coding feature are keyed to each other.

Another arrangement comprises a drug delivery system having a coding system. The drug delivery system includes a drug delivery device, a cartridge, and a collar fitted around the cartridge. In particular, the drug delivery device includes a dose setting mechanism and a cartridge holder removably coupled to the dose setting mechanism. The cartridge is sized and shaped to be contained within the cartridge holder and operably responsive to the dose setting mechanism. Further, the collar comprises a coding feature, where the coding feature is configured to pass through a corresponding coding feature provided by the cartridge holder of the drug delivery device.

In one aspect, a coding system for a drug reservoir, which is intended for use with a reservoir holder of a drug delivery device, comprises a collar fitted around the drug reservoir, wherein the collar comprises a coding feature, and wherein the coding feature is configured to pass through a corresponding coding feature provided by the reservoir holder of the drug delivery device.

In an example embodiment, the collar is fitted around a shoulder of the drug reservoir.

In a further example embodiment, the corresponding coding feature is located near a distal end of the reservoir holder.

In a further example embodiment, the collar comprises at least one protrusion on an inner diameter of the collar, and the at least one protrusion is configured to snap over a ferrule of the cartridge when the collar is fitted to the drug reservoir.

In a further example embodiment, the collar comprises a first portion and a second portion connected to a common hinge.

In a further example embodiment, the collar comprises a flange hinged around its circumference.

In a further example embodiment, the collar is constrained so as not to rotate relative to the drug reservoir.

In a further example embodiment, the collar is constrained with adhesive.

In a further example embodiment, the collar is configured such that it is difficult to remove.

In a further example embodiment, the coding feature comprises at least one of a protrusion and an indentation.

In a further example embodiment, the coding feature comprises at least one protrusion and at least one indentation.

In a further example embodiment, the collar is fitted around the drug reservoir during a manufacturing process.

In a further example embodiment, the collar is fitted around the drug reservoir by a user of the drug delivery device.

In another aspect, a coding system for a drug delivery device comprises a first ring feature comprising a first coding feature, wherein the first ring feature is fitted to a first component of the drug delivery device, and a second ring feature comprising a second coding feature, wherein the second ring feature is fitted to a second component of the drug delivery device, and wherein the first ring feature and the second ring feature are keyed to each other.

In a further example embodiment, the first component of the drug delivery device is a standard 3 milliliter (ml) cartridge and the second component of the drug delivery device is a standard cartridge holder for a standard 3 ml cartridge.

In a further example embodiment, the first component of the drug delivery device comprises a molded cartridge.

In a further example embodiment, the first coding feature comprises a pin, and the second coding feature comprises an indentation configured for receiving the pin.

In a further example embodiment, the first ring is fitted to the first component and the second ring is fitted to the second component such that the first and second coding features align when the first component is connected to the second component.

In a further example embodiment, a coding system for a drug delivery device comprises a ring feature comprising a coding feature, wherein the ring feature is fitted to a first component of the drug delivery device, and wherein the coding feature is keyed to a second component of the drug delivery device.

In another aspect, a drug delivery system comprises a drug delivery device comprising a dose setting mechanism and a cartridge holder removably coupled to the dose setting mechanism, a cartridge sized and shaped to be contained within the cartridge holder and operably responsive to the dose setting mechanism, and a collar fitted around the cartridge, wherein the collar comprises a coding feature, wherein the coding feature is configured to pass through a corresponding coding feature provided by the cartridge holder of the drug delivery device.

In a further example embodiment, the drug delivery system comprises a reusable drug delivery system.

In a further example embodiment, the drug delivery system comprises a non-reusable drug delivery system.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1A:
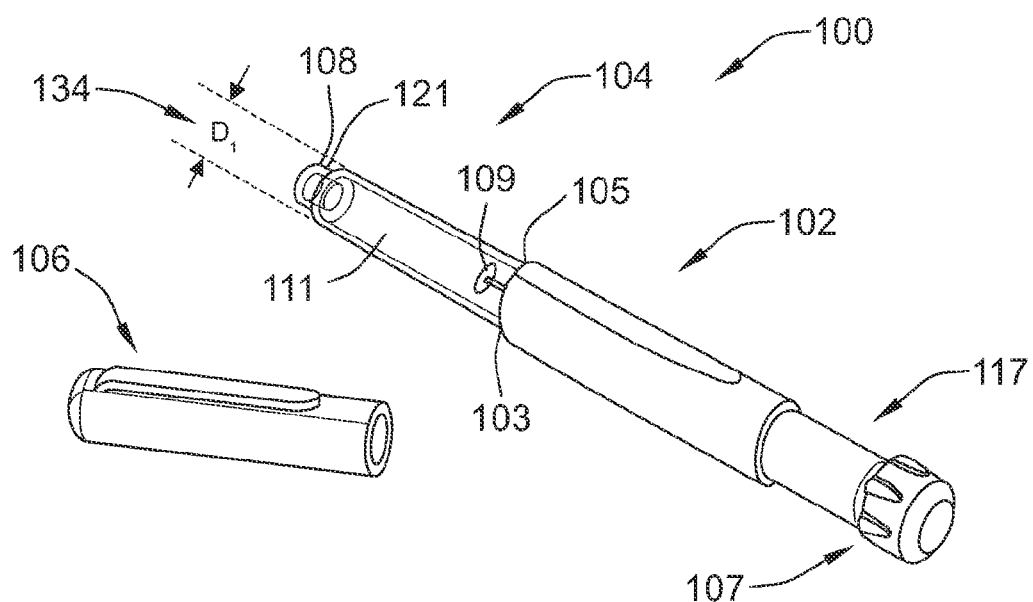
FIG. 1(a) illustrates an exemplary pen type drug delivery device.

Referring to FIG. 1A, there is shown a drug delivery device 100 in the form of a pen type syringe. This drug delivery device 100 comprises a dose setting mechanism 102, a cartridge holder 104, and a removable cap 106. A proximal end 105 of the cartridge holder 104 and a distal end 103 of the dose setting mechanism 102 are removably secured together. The pen type syringe may comprise a re-usable or a disposable pen type syringe. Where the syringe comprises a reusable device 100, the cartridge holder 104 and the dose setting mechanism 102 are removably coupled together. In a disposable device 100, they are permanently coupled together. In FIG. 1, the dose setting mechanism 102 comprises a piston rod 109, such as a threaded piston rod that rotates when a dose is injected.

FIG. 1a illustrates a drug delivery device 100 in the form of a pen type syringe. This drug delivery device 100 comprises a dose setting mechanism 102, a cartridge holder 104, and a removable cap 106. A proximal end 105 of the cartridge holder 104 and a distal end 103 of the dose setting mechanism 102 are removably secured together. The pen type syringe may comprise a re-usable or a disposable pen type syringe. Where the syringe comprises a reusable device, the cartridge holder 104 and the dose setting mechanism are removably coupled together. In a disposable device, they are permanently coupled together. In FIG. 1, the dose setting mechanism 102 comprises a piston rod 109, such as a threaded piston rod that rotates when a dose is injected.

To inject a previously set dose, a double ended needle assembly (not shown) is attached to a distal end 108 of the cartridge holder. Preferably, the distal end of the holder comprises a thread 121 (or other suitable connecting mechanism such as a snap lock, snap fit, form fit, or bayonet lock mechanism) so that the needle assembly may be removably attached to the distal end of the holder. When the drug delivery device is not in use, the removable cap 106 can be releasably retained over the cartridge holder 104.

Figure 1B:
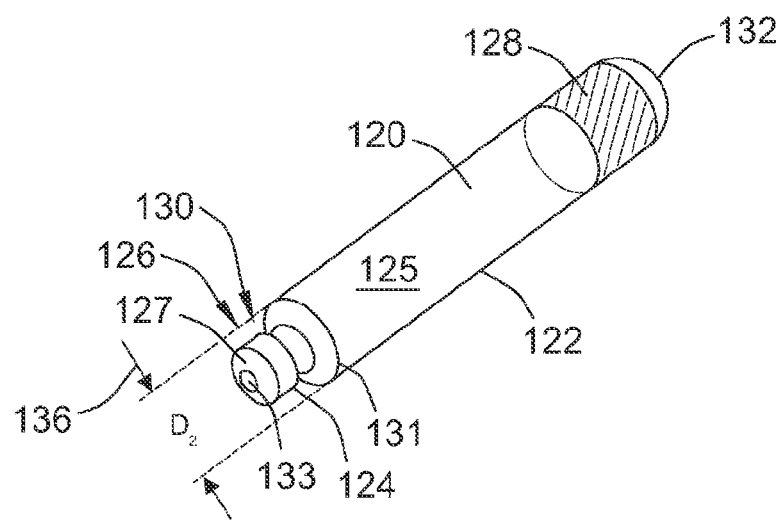
FIG. 1(b) illustrates an exemplary drug cartridge.

An inner cartridge cavity 111 defined by the cartridge holder 104 is dimensioned and configured to securely receive and retain the cartridge 120. FIG. 1b illustrates a perspective view of the cartridge 120 that may be used with the drug delivery device illustrated in FIG. 1a. The cartridge 120 includes a generally tubular barrel 122 extending from a distal end 130 to a proximal end 132. The distal end 130 is defined by an inwardly converging shoulder 131.

At the distal end 130, the cartridge 120 includes a smaller diameter neck 126 and this neck projects distally from the shoulder 131 of the barrel 122. Preferably, this smaller diameter neck 126 is provided with a large diameter annular bead 133 and this bead extends circumferentially thereabout at the extreme distal end of the neck 126. A pierceable seal or septum 127 is securely mounted across the open distal end defined by the neck. The seal 127 may be held in place by a metallic sleeve or ferrule 124. This ferrule 124 may be crimped around the circumferential bead at the distal end of the neck. The medicament 125 is pre-filled into the cartridge 120 and is retained within the cartridge, in part, by the pierceable seal 127, the metallic sleeve 124, and the stopper 128. The stopper 128 is in sliding fluid-tight engagement with the inner tubular wall of the barrel 122. Axially directed forces acting upon the stopper 128 during dose injection or dose administration urges the medication 125 from the cartridge though a double ended needle mounted onto the distal end 130 of the cartridge holder 104 and into the injection site. Such axial forces may be provided by the piston rod 109.

A portion of the cartridge holder 104 defining the cartridge holder cavity 111 is of substantially uniform diameter represented in FIG. 1a by D1 134. This diameter D1 134 is preferably slightly greater than the diameter D2 136 of the cartridge 120. The interior of the cartridge holder includes an inwardly-extending annual portion or stop that is dimensioned to prevent the cartridge 120 from moving within the cartridge holder 104. In this manner, when the cartridge 120 is loaded into the cavity 111 of the cartridge holder 104 and the cartridge holder 104 is then connected to the dose setting member 102, the cartridge 120 will be securely held within the cartridge cavity. More particularly, the neck 126 and ferrule 124 of the cartridge 120 are inserted in a proximal to distal direction into the open proximal end of the cartridge holder 104 with the ferrule eventually passing entirely into the holder 104. With the holder 104 removably coupled to the dose setting mechanism 102, the proximal end of the cartridge 120 will typically abut a stop provided by the dose setting member 102.

A number of doses of a medicament 125 may be dispensed from the cartridge 120. It will be understood that the cartridge 120 may contain a type of medicament that must be administered often, such as one or more times a day. One such medicament is insulin. A movable piston 128 is retained in a first end or proximal end of the cartridge 120 and receives an axial force created by the piston rod 109 of the dose setting mechanism 102.

The dose setting mechanism 102 comprises a dose setter 117 at the proximal 107 end of the dose setting mechanism. In one preferred arrangement, the dose setter 117 may extend along the entire length of the dose setting mechanism. The dose setter 117 may be rotated by a user so as to set a dose.

To administer a dose that may be set by rotating the dose setter 117, the user attaches the needle assembly comprising a double ended needle on the distal end of the cartridge holder. In this manner, the needle assembly pierces the seal 127 of the cartridge 120 and is therefore in liquid communication with the medicament 125. The user pushes on the dose setter 117 to inject the set dose. The same dose setting and dose administration procedure is followed until the medicament 125 in the cartridge is expended and then a new cartridge must be loaded in the device. To exchange an empty cartridge, the user is called upon to remove the cartridge holder 104 from the dose setting mechanism 102.

A coding system for use with a drug delivery system, such as drug delivery device 100, is provided. In an example of the invention, a coding system for a drug reservoir intended for use with a reservoir holder, such as drug cartridge 122 and cartridge holder 104, is provided. Generally, the coding system includes a collar fitted around the drug reservoir, and the collar comprises a coding feature. This coding feature is configured to pass through a corresponding coding feature provided by the reservoir holder of the drug delivery device.

Figure 2A:
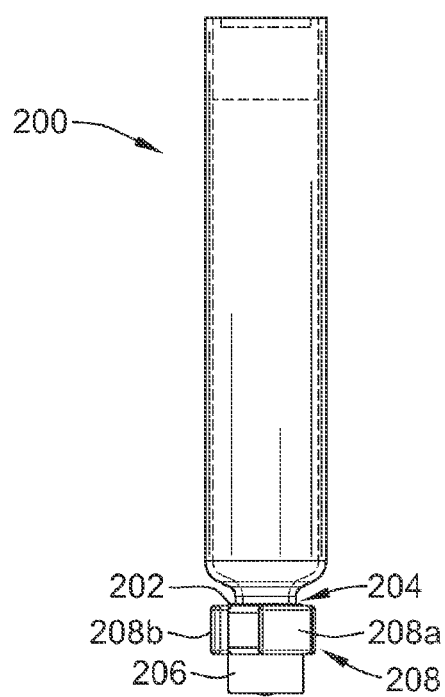
FIG. 2(a) is a cross-sectional view of an example drug cartridge having an example collar fitted to the drug cartridge.
Figure 2B:
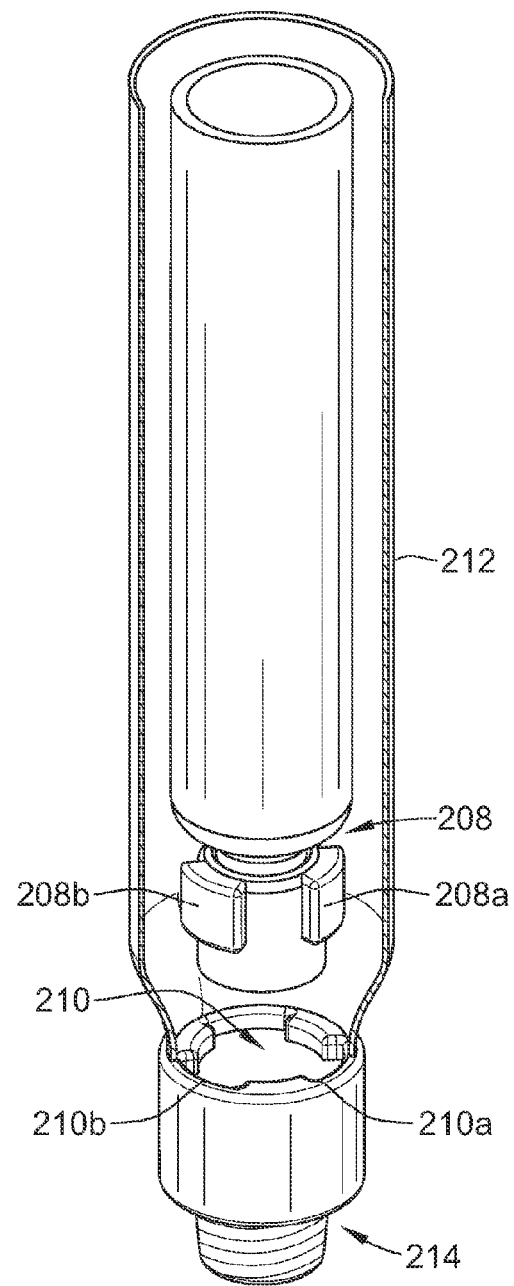
FIG. 2(b) is a perspective view of the drug cartridge having a fitted collar of FIG. 2(a) and an example cartridge holder.

FIGS. 2(a) and 2(b) depict an example drug cartridge having an example coding system. In particular, FIG. 2(a) shows a drug cartridge 200 with a collar 202 fitted to it. In this example, the collar 202 is fitted to a shoulder 204 of the cartridge and just above the ferrule 206 of the cartridge. The collar 202 includes a coding feature 208. This coding feature is configured to pass through a corresponding coding feature 210 provided by the reservoir holder 212 of a drug delivery device. In this example, the corresponding coding feature is provided toward the distal end 214 of the reservoir holder 212. However, it should be understood that both the collar 202 and corresponding coding feature 210 may be located in any suitable location.

The coding feature 208 of collar 202 comprises one or more protrusions along the outer circumference of the collar. In the example embodiment shown in FIGS. 2(a) and 2(b), there are three protrusions along the outer circumference of the collar. In particular, the coding feature includes protrusions 208a, 208b, and a third protrusion (not shown). Corresponding coding feature 210 includes corresponding indentations 210a, 210b. As seen in FIG. 2(b), the indentations are substantially the same size and shape as the protrusions 208a, 208b, and thus the protrusions 208a, 208b may pass through indentations 210a, 210b when the cartridge 200 is inserted into the holder 212. Further, as can be seen from FIG. 2(b), a cartridge will only fit into the coded holder 212 if the coding feature of the collar (e.g., the protrusions) is able to pass through the corresponding coding feature of the holder (e.g., the indentations).

The embodiment of FIGS. 2(a) and 2(b) comprises the features of:
 a drug cartridge 200 with a collar 202 fitted to a shoulder 204 of the cartridge just above the ferrule 206 of the cartridge;
 the collar 202 comprising a coding feature 208;
 the coding feature 208 being configured to pass through a corresponding coding feature 210 provided by a reservoir holder 212 of the drug delivery device;
 the coding feature 208 comprising protrusions along an outer circumference of the collar 202; and
 the corresponding coding feature 210 comprising indentations 210a, 210b of substantially the same size and shape as the protrusions 208a, 208b, so that the protrusions 208a, 208b pass through the indentations 210a, 210b when the cartridge 200 is inserted into the holder 212.

Many different coding features are possible. As mentioned above with respect to FIGS. 2(a) and 2(b), the collar coding feature may include one or more protrusions, and the corresponding coding feature of the reservoir holder may include an indentation or indentations to accommodate the one or more protrusions; however, vice versa is also possible. That is, the collar coding feature may include one or more indentations, and the corresponding coding feature of the reservoir holder may include a protrusion or protrusions coded to the one or more indentations. Still alternatively, the collar coding feature may include both at least one protrusion and at least one indentation.

Generally, any type of coding features may be incorporated into the collar and the corresponding holder coding feature. For instance, the coding features may include a plurality of code elements (e.g., protrusions). In addition, the coding feature elements may vary in size, cross-sectional shape, and position. For example, the axial extent, circumferential extent, radial extent, cross-section shape (in any plane, e.g., longitudinal or traverse) of the protrusions may be varied. The size of each protrusion may be different from the others. For example, there may be a number of different protrusions with different radial extents. Regarding varying the cross-section shape, a coding system may consist of a number of coding features, each of which is smaller in one area and larger in another than all of the other coding features of the system. In another example, the holder and cartridge may comprise unique alignment features.

It should be appreciated from the above that collars in accordance with the invention may include a wide variety of different coding features. Accordingly, a large number of coding schemes are possible, and a large number of cartridges may easily be distinguished from one another.

A collar in accordance with an example of the invention may be connected to a reservoir in various ways. In a first example, the collar may include at least one protrusion (not shown) on an inner diameter of the collar, wherein the protrusions are configured to snap over a ferrule of the cartridge when the collar is fitted to the cartridge. In a second example, the collar comprises a first portion and a second portion, wherein the first and second portions are connected to a common hinge. The first and second portions may comprise corresponding snap-fit features. The hinged portions may then be wrapped around a portion of the cartridge and then may be snapped together. In a third example, an inwardly directed flange is connected to the collar by a hinge around its circumference, and has an inner diameter smaller than the diameter of the ferrule. During assembly, the flange hinges outwards to allow the collar to be pushed over the ferrule, then hinges back into the recess under the ferrule hence retaining the collar. Other examples of how a collar is attached to a cartridge are possible as well.

In addition, a collar in accordance with the invention may be attached to a drug reservoir at various times. For instance, the collar may be fitted around the drug reservoir during a manufacturing process. Alternatively, the collar may be fitted around the drug reservoir after the reservoir has been shipped to customers. For example, the collar may be fitted around the drug reservoir by a user, such as a doctor, nurse, or patient.

In another example, the collar is constrained so as to not rotate relative to the cartridge. The collar may be constrained in a variety of ways. For example, the color may be constrained with adhesive, such as glue. Constraining the collar may beneficially stabilize the cartridge when the cartridge is inserted into a cartridge holder, helping the user to align coding on the collar and the coding feature to which it is mated.

According to another embodiment of the invention, a coding system having a coding ring or rings may be fitted to standard drug delivery device components. It should be understood that a standard drug delivery device component may be any standard drug delivery device component now known in the art or later developed. For the purpose of this disclosure a standard drug delivery device component is a component that may be used with other drug delivery device components for which the given component is not intended to be used with. Examples of standard drug delivery components include but are not limited to a standard 3 ml cartridge and a standard 3 ml cartridge holder.

Alternatively, the cartridge may be molded and include features to retain a coding ring. Fastening features may be included on the molded cartridge, or on the coding ring, to allow the cartridge to be connected to the drug delivery device without the use of a cartridge holder.

Beneficially, the coding rings in accordance with the invention may prevent a standard component from being used with other standard components for which it is not intended. Thus, standard components may be coded to one another. In an example, a coding system in accordance with the invention may include a plurality of ring features. Specifically, a coding system for a drug delivery device may include a first ring feature comprising a coding feature, where the first ring feature is fitted to a first component of the drug delivery device. Further, the coding system may include a second ring feature comprising a second coding feature, where the second ring feature is fitted to a second component of the drug delivery device. The first ring feature and the second ring feature are keyed to each other.

In another example of this embodiment, a coding system may include a single ring fitted to a standard component. In this example, the coding system may include a ring feature comprising a coding feature, where the ring feature is fitted to a first component of the drug delivery device, and where the coding feature is keyed to a second component of the drug delivery device. In yet another example, a coding system for a drug delivery device may include three or more rings, each ring fitted to three or more components.

Figure 3:
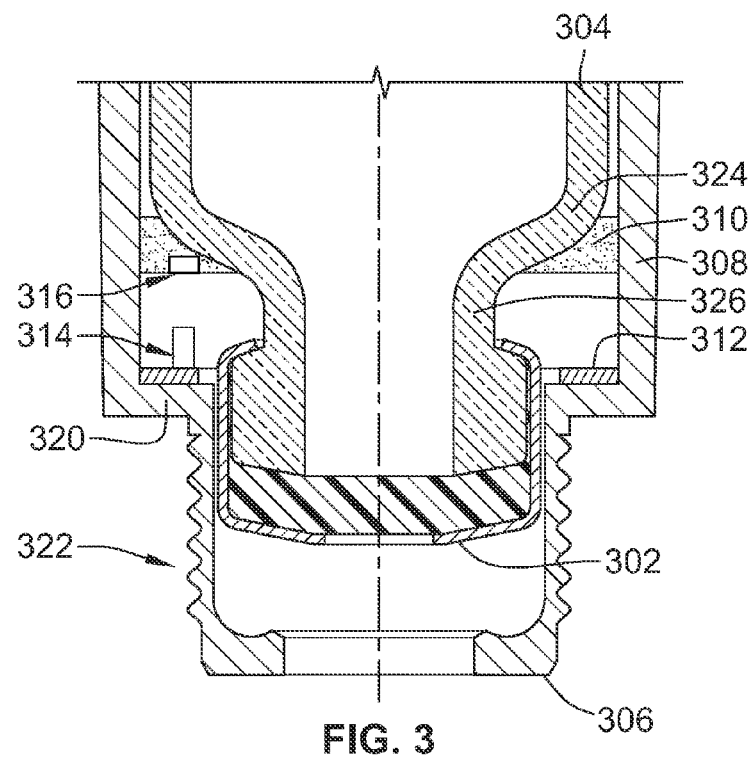
FIG. 3 is a cross-sectional view of an example coding system in accordance with the proposed concept.
Figure 4:
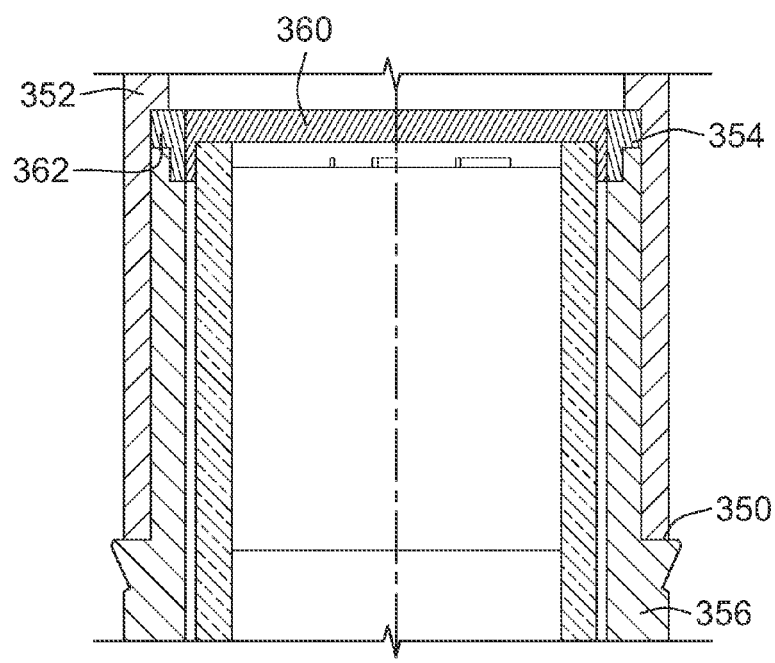
FIG. 4 is a cross-sectional view of another example coding system in accordance with the proposed concept.

Examples of the ring feature coding system are shown in FIGS. 3 and 4. First, with reference to FIG. 3, a coding system with two rings for coding a holder to a cartridge is shown. FIG. 3 is a cross-sectional view of a distal end 302 of a standard drug cartridge 304 and a distal end 306 of a standard cartridge holder 308. The proximal ends (not shown) of the cartridge 304 and the holder 308 would include the same or similar features as the proximal ends of the cartridge and holder of FIGS. 1(a) and 1(b).

Drug cartridge 304 has a first ring feature 310 fitted to it, and cartridge holder 308 has a second ring feature 312 fitted to it. As shown in FIG. 3, ring feature 312 has a coding feature 314 and ring feature 310 has a corresponding coding feature 316. In this example, coding feature 314 is a protrusion in the form of a pin, and coding feature 316 is a coding feature in the form of an indentation sized and shaped to fit the pin 314. It should be understood that these are merely example coding features, and the coding features may be keyed to one another in any suitable fashion.

Ring feature 312 is fitted to a base 320 of the cartridge holder 308. The base 320 is the internal base located above the connection means 322 of the holder. This ring 312 may be attached to the base 320 in various ways, including, for example, with an adhesive. Ring feature 310 is fitted to the shoulder 326 of the drug cartridge 304, especially to the proximal end 324 of the shoulder 326 of the drug cartridge 304. This ring feature may also be attached to a drug delivery system component in various ways, including, for example, with an adhesive.

After the coding ring features are fitted to the components, the cartridge 304 and holder 308 are coded to one another. When the cartridge 304 is inserted into holder 308, the pin 314 will fit in indentations 316, and thus the cartridge 304 may be fully inserted into the holder 308.

The embodiment of FIG. 3 comprises the features of:
 a drug cartridge 304 having a shoulder 326;
 a first ring feature 310 fitted to the shoulder 326 of the cartridge 304;
 a cartridge holder 308 having a base 320;
 a second ring feature 312 fitted to the base 320 of the cartridge holder 308;
 a protrusion in the form of a pin 314 of the second ring feature 312; and
 an indentation 316 in the first ring feature 310 sized and shaped to fit the pin 314;
 wherein the pin 314 fits in the indentation 316 when the cartridge 304 is inserted into the holder 308.

Given the coding features in accordance with the concept, if the coding features of a first drug delivery system component and a second drug delivery device component are not matched (i.e., keyed or complementary to one another), the two parts cannot be assembled together. Preferably, the coding features of a first ring feature fitted to a first component only match those of a second ring feature fitted to a second component when the first component is intended to be used by that second component. Thus, with an incorrect combination of components, the user is alerted at an early stage of assembly that the components are not intended for use with one another.

The coding rings may be fitted to the drug delivery device component features at various stages. For instance, the coding rings may be fitted during the manufacture of the components. As another example, a user of the components of the drug delivery device may fit these coding rings. For instance, a doctor, pharmacist, nurse, or user may fit these coding rings to various drug delivery device components.

The coding rings may be manufactured by any suitable method or from any suitable material, for example they may be injection molded polymers such as PP, HDPE, PBT, or ABS. They may be attached to the other components by any means such as snap-fit features or glue.

FIG. 4 shows an example of a coding system including a single ring feature. In particular, this figure depicts a coding system for coding a holder to a dose setting mechanism of a drug delivery device. FIG. 4 shows a distal end 350 of a dose setting mechanism 352 of a device when connected to a proximal end 354 of a cartridge holder 356. The dose setting mechanism 352 has a coding ring 360 fitted to it, and this coding ring 360 includes a coding feature 362. The coding feature 362 is a protrusion, which is configured for interacting with the proximal end 354 of the cartridge holder. If the coding feature was not properly keyed to the proximal end of the cartridge holder, the holder may not be able to properly connect to the dose setting mechanism. Thus, the coding ring helps code the standard dose setting mechanism to the standard cartridge holder.

The embodiment of FIG. 4 comprises the features of:
a dose setting mechanism 352 having a distal end 350;
a cartridge holder 356 having a proximal end 354;
wherein the distal end 350 of the dose setting mechanism 352 is connected to the proximal end 354 of the cartridge holder 356;
a coding ring 360 fitted to the dose setting mechanism 352; and
the coding ring 360 comprising a coding feature 362, which is a protrusion configured for interacting with the proximal end 354 of the cartridge holder 356.

It should be understood that the coding rings in accordance with the invention may beneficially be used to code a wide variety of drug delivery device components. For example, one or more rings may be used to code the following adjacent parts: (i) drug reservoir to holder (either at distal end or proximal end of the reservoir); (ii) reservoir to device (e.g., dose setting mechanism) (e.g., with an adaptor on a sidewall); (iii) holder to device; (iv) cap to reservoir; (v) cap to holder; (vi) cap to device. Other examples are possible as well.

In another example, a coding system for a drug delivery system may include coding for multiple adjacent drug delivery device components. For instance, a drug delivery device may include both coding systems shown in FIGS. 3 and 4.

Although aimed primarily at the insulin market, the proposed coding schemes may apply to other drugs. The coding system may apply to various devices, including the following examples:

a. An injector pen with a cartridge (e.g. 3 ml cylindrical glass cartridge) and a separate cartridge assembly.

b. An injector pen with a cartridge (e.g. 3 ml cylindrical glass cartridge) non removably retained in a cartridge assembly, so that the assembly will be disposed of with the primary pack.

c. An injector pen where the primary pack attaches directly to the pen, e.g. an injection moulded polymer cartridge.

d. Any drug delivery device, with any type of primary pack, e.g. inhaler, pouch.

Figure 5:
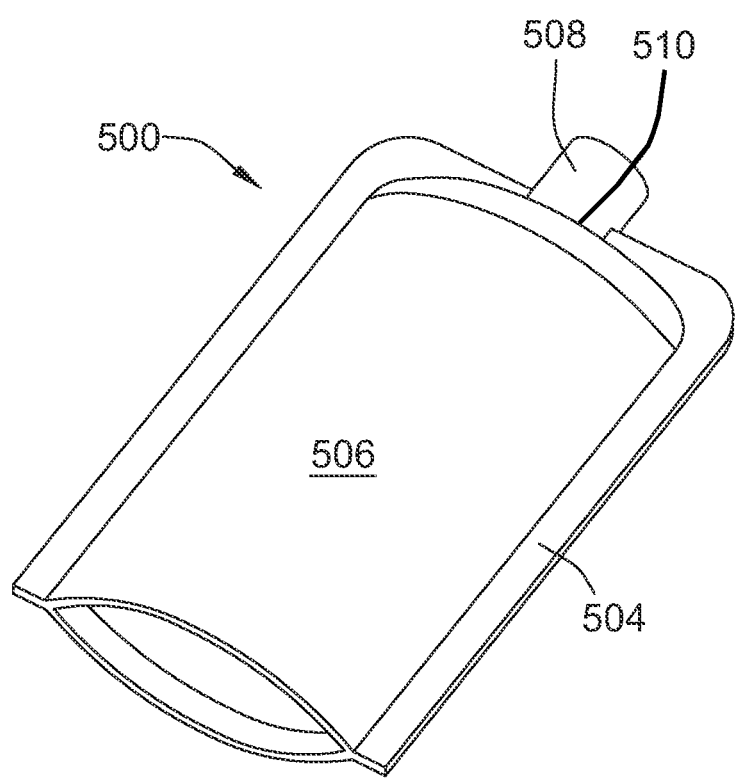
FIG. 5 is a perspective view of an exemplary drug reservoir that may be coded in accordance with the proposed concept.

An example primary pack is shown in FIG. 5. FIG. 5 illustrates a drug reservoir 500 comprising a vessel 504 that contains a medicament 506. A stopper 508 is provided along a distal end of the vessel and is attached to the vessel so as to prevent the medicament 506 from exiting the vessel 504. The coding described above may be provided on the output port 510 of the vessel.

Further, although the proposed coding system has been described with reference mainly to a cartridge assembly and a dose setting mechanism, the proposed system may apply to any location on any components of a drug delivery system. For instance, the coding system may apply in the following examples:

a. The interface between a cartridge (or a feature attached to the cartridge) and its holder;

b. The interface between a cartridge (or a feature attached to the cartridge) and the drug delivery device; and c. The interface between a cartridge assembly, a molded cartridge assembly, or other primary pack and the drug delivery device.

Still further, a collar or ring feature in accordance with the invention may be fitted so that it is difficult for a user to remove. For example, it may be attached using snap-fit features, where the angle of contact faces allow easy assembly but difficult removal. Since the collar or ring feature may be difficult to remove, it would beneficially be difficult for a user to move the collar or ring to a different cartridge or other drug delivery system feature.

The proposed coding system results in a number of advantages. For example, the proposed coding system help to assist a user to ensure that a given drug delivery device component is only attached to a drug delivery device component for which it is intended. The coded system also results in a low cost coding mechanism since the proposed collars and holders do not require a large number of parts and can be manufactured in a cost effective manner. Moreover, there are quite a large number of different coding configurations between the holder and the dose setting mechanism that may be used. Consequently, with proposed coding schemes, a large number of medicaments can be distinguished from one another.

In given embodiments, the coding may be designed to block all incorrect reservoirs from being inserted into an inccorrect cartridge holder. In alternative embodiments, the coding may be designed to block reservoirs of a given type, but not all types of reservoirs. For example, in an embodiment, the coding may block only reservoirs not intended for the housing and that comprise dangerous drugs. For instance, a short-acting drug could be fitted into a device intended for long-acting drugs, but not vice versa. As another example, a low concentration drug could be fitted into a device intended for high concentration drugs, but not vice versa.

The invention claimed is:

1. A coding system for a drug delivery device, comprising:

a collar comprising a first coding feature of a component of the drug delivery device, wherein the component of the drug delivery device is a cartridge having a tubular barrel extending from a distal end to a proximal end, wherein the distal end is defined by an inwardly converging shoulder with the collar fitted to the shoulder, and wherein the collar is constrained so as to not rotate relative to the cartridge;

a cartridge holder having a cavity configured to securely receive and retain the cartridge, wherein an inner diameter of the cavity of the cartridge holder is greater than an outer diameter of the proximal end of the barrel, wherein a distal end of the cartridge holder has a connecting mechanism configured to attach to a needle assembly, wherein the connecting mechanism comprises one of a thread, a snap lock, a snap fit or bayonet lock mechanism, and wherein the cartridge holder further includes a ring feature comprising a second coding feature, wherein the first coding feature and the second coding feature are keyed to each other, wherein the first coding feature is configured to pass through the second coding feature along one of a distal direction and a proximal direction, and wherein the component and the cartridge holder are configured to be correctly assembled only when the first coding feature and the second coding feature match, wherein the first coding feature comprises at least one of a protrusion and an indentation along an outer circumference of the collar, and wherein the second coding feature comprises at least one of an indentation and a protrusion, wherein the at least one protrusion or indentation of the first coding feature is substantially the same size and shape as the at least one corresponding indention or protrusion of the second coding feature.

2. The coding system of claim 1, further comprising
the first coding feature comprising protrusions along an outer circumference of the collar; and
the second coding feature comprising indentations of substantially the same size and shape as the protrusions, so that the protrusions pass through the indentations along the distal direction or the proximal direction when the cartridge is inserted into the cartridge holder.

3. The coding system of claim 1, wherein the collar is provided to be fitted around the cartridge by a user of the drug delivery device.

4. The coding system of claim 1, wherein the second coding feature has a longitudinal axis parallel to a longitudinal axis of the cartridge holder.

5. A drug delivery system, the system comprising:
a drug delivery device comprising a dose setting mechanism and a cartridge holder removably coupled to the dose setting mechanism, wherein the cartridge holder has a cavity configured to securely receive and retain a cartridge, wherein a distal end of the cartridge holder has a connecting mechanism configured to attach to a needle assembly, wherein the connecting mechanism comprises one of a thread, a snap lock, a snap fit or bayonet lock mechanism;
wherein the cartridge is sized and shaped to be contained within the cartridge holder and operably responsive to the dose setting mechanism,
wherein the cartridge comprises a tubular barrel extending from a distal end to a proximal end of the cartridge and wherein the distal end of the cartridge is defined by an inwardly converging shoulder, wherein an inner diameter of the cavity of the cartridge holder is greater than an outer diameter of the proximal end of the barrel, and
a collar fitted around the inwardly converging shoulder of the cartridge, wherein the collar comprises a first coding feature, wherein the first coding feature is configured to pass through a corresponding second coding feature provided by the cartridge holder of the drug delivery device, along one of a distal direction and a proximal direction, and wherein the collar is constrained so as to not rotate relative to the cartridge,
wherein the cartridge and the cartridge holder are configured to be correctly assembled only when the first coding feature and the second coding feature match,
wherein the first coding feature comprises at least one of a protrusion and an indentation along an outer circumference of the collar, and
wherein the second coding feature comprises at least one of an indentation and a protrusion,
wherein the at least one protrusion or indentation of the first coding feature is substantially the same size and shape as the at least one corresponding indention or protrusion of the second coding feature.

6. The drug delivery system of claim 5, wherein the drug delivery system comprises a reusable drug delivery system.

7. The drug delivery system of claim 5, wherein the drug delivery system comprises a non-reusable drug delivery system.

8. The drug delivery system of claim 5, wherein the second coding feature has a longitudinal axis parallel to a longitudinal axis of the cartridge holder.

9. A coding system for a drug delivery device, comprising:
a first ring feature comprising a first coding feature of a component of the drug delivery device, wherein the component of the drug delivery device is a cartridge having a tubular barrel extending from a distal end to a proximal end, wherein the distal end is defined by an inwardly converging shoulder with a collar comprising the first coding feature fitted to the shoulder;
a cartridge holder having a cavity configured to securely receive and retain the cartridge, wherein an inner diameter of the cavity of the cartridge holder is greater than an outer diameter of the proximal end of the barrel, wherein a distal end of the cartridge holder has a connecting mechanism configured to attach to a needle assembly, wherein the connecting mechanism comprises one of a thread, a snap lock, a snap fit or bayonet lock mechanism, and wherein the cartridge holder further includes a second ring feature comprising a second coding feature, wherein the second coding feature has a longitudinal axis parallel to a longitudinal axis of the cartridge holder, wherein the first coding feature and the second coding feature are keyed to each other, and wherein the component and the cartridge holder are configured to be correctly assembled only when the first coding feature and the second coding feature match, and
wherein the collar is constrained so as to not rotate relative to the cartridge.

\* \* \* \* \*